United States Patent
Franchi

[19]

[11] Patent Number: 6,030,335
[45] Date of Patent: Feb. 29, 2000

[54] IMPLANTABLE HEART-ASSIST PUMP OF THE BACK-PRESSURE BALLOON TYPE

[75] Inventor: Pierre Franchi, Vitry sur Seine, France

[73] Assignee: Synthelabo Biomedical, France

[21] Appl. No.: 09/117,324

[22] PCT Filed: Dec. 30, 1996

[86] PCT No.: PCT/FR96/02104

§ 371 Date: Jan. 27, 1999

§ 102(e) Date: Jan. 27, 1999

[87] PCT Pub. No.: WO97/26929

PCT Pub. Date: Jul. 31, 1997

[30] Foreign Application Priority Data

Jan. 26, 1996 [FR] France ................................. 96 00949

[51] Int. Cl.$^7$ ........................................................ A61M 1/12
[52] U.S. Cl. .................................................................. 600/16
[58] Field of Search ................................ 600/16, 17, 18; 623/3

[56] References Cited

U.S. PATENT DOCUMENTS

| | | | |
|---|---|---|---|
| 3,668,708 | 6/1972 | Tindal | 623/3 |
| 4,276,874 | 7/1981 | Wolugk | 600/18 |
| 4,888,011 | 12/1989 | Kung et al. | 623/3 |
| 5,171,207 | 12/1992 | Whalgw | 600/76 |

*Primary Examiner*—William E. Kamm
*Attorney, Agent, or Firm*—Fish & Richardson P.C.

[57] ABSTRACT

The pump comprises: an essentially rigid body open at both ends and designed to be inserted in the down aorta artery; a flexible and elastic membrane (18) in the form of a sleeve connected in sealed manner to the body at the periphery of the ends thereof so as to define firstly, between the body and the sleeve, a closed intermediate space (20) of variable volume, and secondly, inside the sleeve, a variable volume (22) through which the blood to be pumped passes; and means for connecting the intermediate space to a source of hydraulic fluid suitable for causing the membrane to pass from a free state to a tensioned state in which it is urged radially inwards, thereby correspondingly reducing the volume through which the blood passes, and vice versa. According to the invention, between the ends of the body, the membrane is freely movable relative to the body; and the membrane has at least three longitudinal stiffener elements (36) uniformly distributed around the periphery of the membrane, said stiffener elements being suitable for locally reducing the longitudinal elasticity of the membrane, imposing a star-shape to the right section of the membrane in the tensioned state, which shape develops progressively between each end region and the middle region, said star-shape leaving a residual volume without the membrane coming into contact against itself.

11 Claims, 2 Drawing Sheets

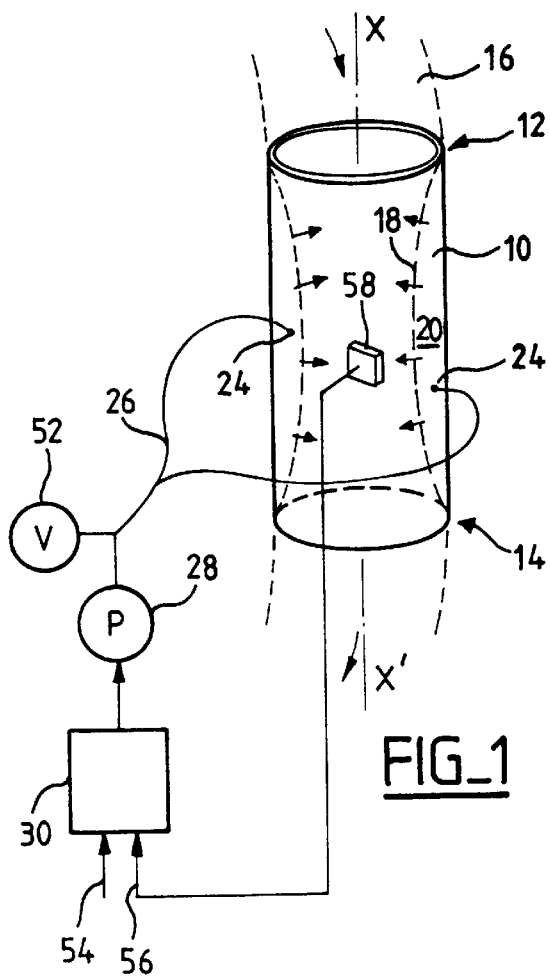
FIG_1
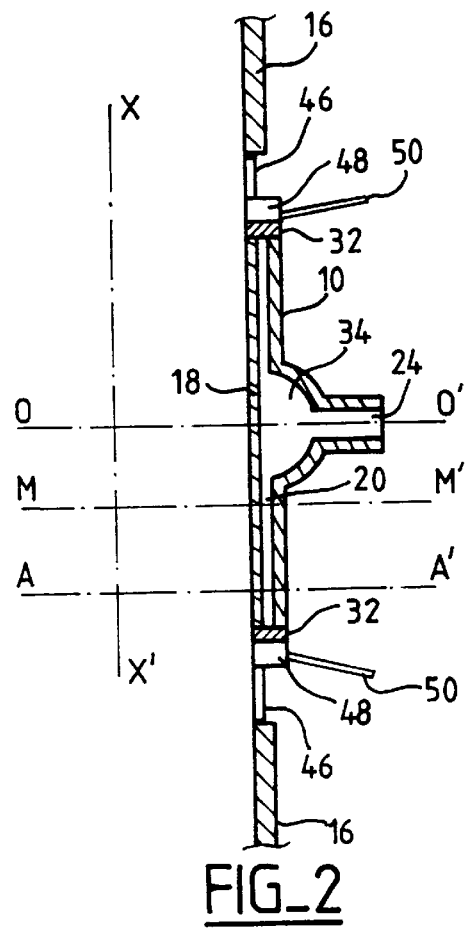
FIG_2
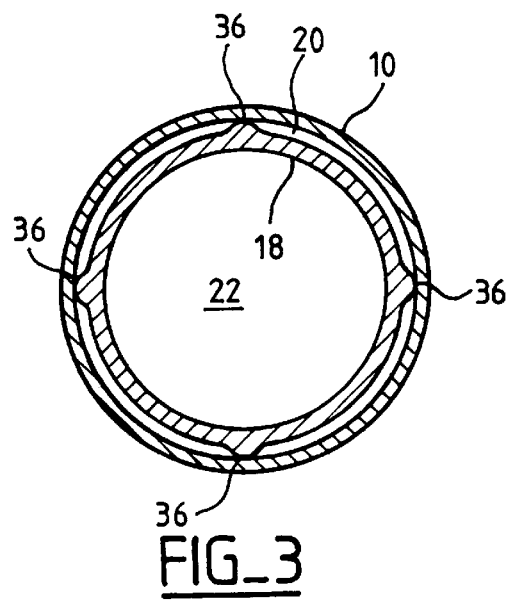
FIG_3
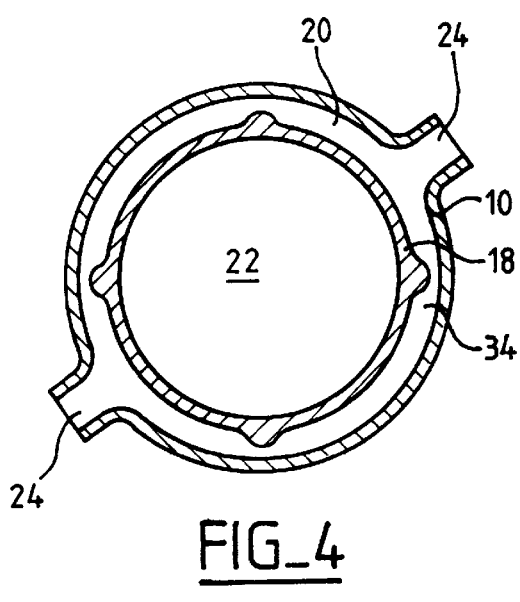
FIG_4

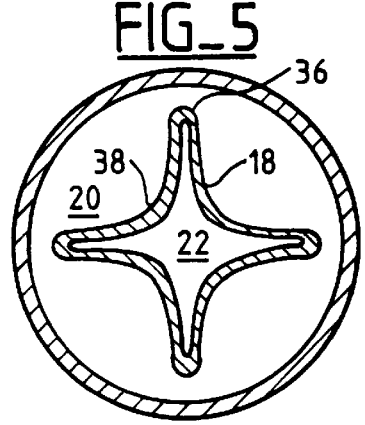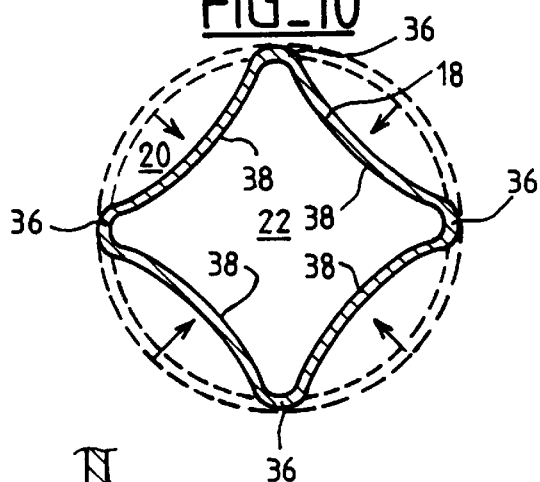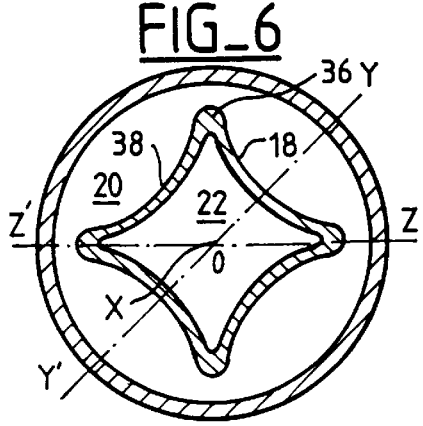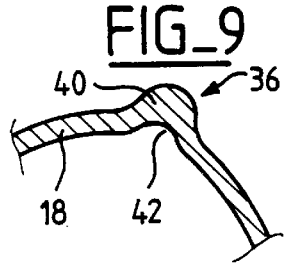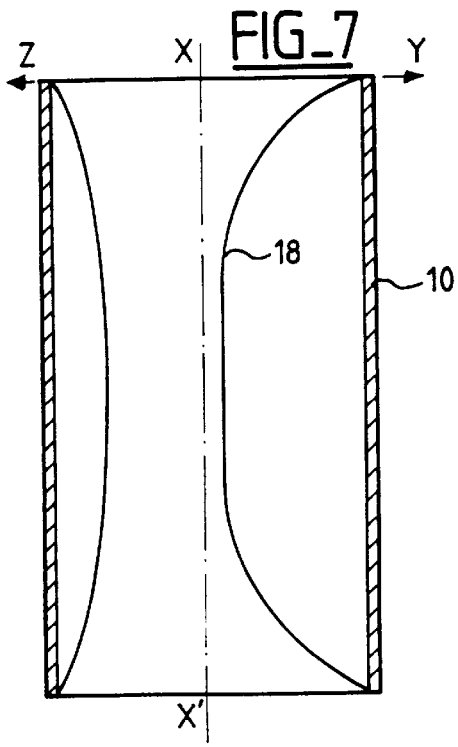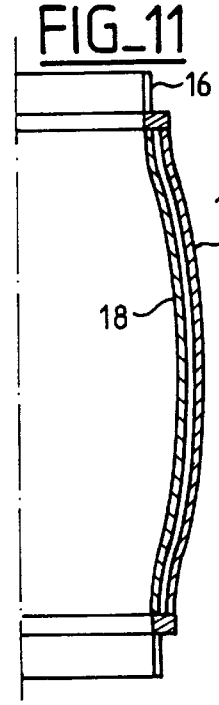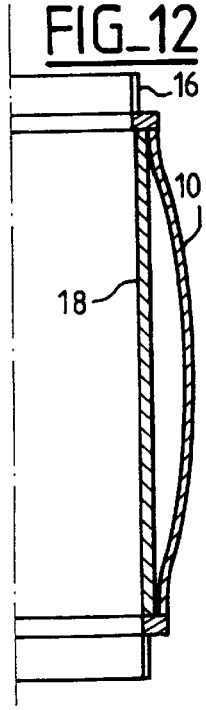

IMPLANTABLE HEART-ASSIST PUMP OF THE BACK-PRESSURE BALLOON TYPE

This is a continuation of International Patent Application No. PCT/FR96/02104, with an international filing date of Dec. 30, 1996, now pending.

The invention relates to an implantable heart-assist pump of the back-pressure balloon type.

The back-pressure intra-aortic balloon technique is well known for providing effective hemodynamic assistance to the left ventricle in the event of congestive heart failure: the balloon which is inserted in the down branch of the aorta is inflated during the diastolic phase of the heart beat cycle, and as a result it injects an additional volume of blood into the arterial network upstream and downstream from its position. Deflated during the following systole of the heart, it decreases the load on the left ventricle and thus makes it possible to increase blood flow. The hemodynamic balance is positive: an increase in the ejection fraction, and a decrease in the telediastolic pressure. In this way, the balloon delivers additional energy which the ventricle is no longer capable of supplying, and the state of the patient is very significantly improved.

Implanted systems have already been proposed enabling said technique to be implemented in entirely self-contained manner, as described for example in U.S. Pat. No. 5,222,980.

That document describes a permanent implantable heart-assist pump inserted in the down aorta, operating on the above-described principle of the back-pressure balloon, and constituted by a flexible and elastic membrane in the form of a sleeve whose axis coincides with that of the aorta and disposed in and replacing a segment of aorta that has been removed. The membrane is contained in a rigid chamber that has substantially the same shape as the membrane at rest, and into which hydraulic fluid is injected from an external generator for the purpose of compressing the membrane and thus reducing the volume of blood that it contains. Conversely, extracting the fluid increases the inside volume and thus fills the pump.

One of the problems encountered in the design of appliances of that type lies in the extremely high level of reliability that they must provide, given that they are implanted. Operating for a duration of five years corresponds to about 300,000,000 cycles, and all of the elements of the implanted system must be capable of being subjected to those cycles without damage and without failure.

To this end, selecting the material for the flexible membrane and defining it become critical aspects of the design of an implantable heart-assist pump.

In addition to a lifetime compatible with long term implantation, it is also essential for the pump to be designed in such a manner as to minimize any risk of incidents of thrombosis, and that constitutes one of the major difficulties presented by cardiovascular prostheses.

To this end, the organization of the pump, and in particular the way in which its flexible membrane is defined, must satisfy the following conditions:

roughnesses, turbulence, cavities, and stasis that could generate thrombosis must be reduced;

any compression and friction in the zones of contact between different parts of the membrane or between the membrane and surrounding structures must be eliminated since they give rise to hemolysis;

the inside space of the membrane must be flushed completely by the flow of blood on each heart systole; and the membrane must operate in combination with local and continuous pharmacological treatment opposing thrombotic and expansive processes, without prejudicing treatment of the inside surface to encourage colonization by autogenous endothelial cells.

One of the objects of the invention is to provide an implantable heart-assist pump enabling all of the above-explained constraints and conditions to be satisfied by a special organization of the various elements of the pump, and most particularly of the flexible membrane.

The pump is of the above-specified known type, i.e. it comprises: an essentially rigid body open at both ends and designed to be inserted in the down aorta artery; a flexible and elastic membrane in the form of a sleeve connected in sealed manner to the body at the periphery of the ends thereof so as to define firstly, between the body and the sleeve, a closed intermediate space of variable volume, and secondly, inside the sleeve, a variable volume through which the blood to be pumped passes; and means for connecting the intermediate space to a source of hydraulic fluid suitable for causing the membrane to pass from a free state to a tensioned state in which it is urged radially inwards, thereby correspondingly reducing the volume through which the blood passes, and vice versa.

According to the invention, between the ends of the body, the membrane is freely movable relative to the body; and the membrane has at least three longitudinal stiffener elements uniformly distributed around the periphery of the membrane, said stiffener elements being suitable for locally reducing the longitudinal elasticity of the membrane, imposing a star-shape to the right section of the membrane in the tensioned state, which shape develops progressively between each end region and the middle region, said star-shape leaving a residual volume without the membrane coming into contact against itself.

According to various other advantageous characteristics:

the longitudinal stiffener elements are locally dimensioned so as to ensure that the elongation percentage of the membrane material in the tensioned state is limited at all points to a predetermined limit value as a function of the extreme profile taken up by the membrane in said state; these longitudinal stiffener elements are preferably ribs formed on the outside face of the membrane, with the membrane's inside face including a preformed concave shape in register with said ribs;

the membrane further includes transverse stiffener elements suitable for locally reducing the transverse elasticity of the membrane;

the body further includes at least one peripheral annular enlargement in the form of an annular channel open towards the membrane and connected to at least one duct for delivering hydraulic fluid;

the body is a right circular cylinder and the membrane in the free state is similar in shape to the body, or indeed is in the form of a body of revolution having an outwardly curved generator line so as to present a middle region of greater diameter than the end regions; in which case the membrane in the free state may either be circularly symmetrical, matching the shape of the body, or else it may be in the form of a right cylinder;

means are also provided for controlled injection of a pharmaceutical agent for opposing thromboses and expansive processes that may occur locally; and the hydraulic fluid is a biocompatible and isotonic fluid, and a percutaneously-accessible container is provided together with means for adjusting the volume of the fluid and/or its salinity and optionally for emptying said fluid and/or discharging it into the body of the patient, should that be necessary.

An embodiment of the invention is described below with reference to the accompanying drawings.

FIG. 1 is a diagrammatic view showing the various members constituting the pump of the invention.

FIG. 2 is a longitudinal half-section of the assembly comprising the body and the membrane, which assembly occupies the place of the segment of aorta that has been removed.

FIG. 3 is a cross-section on MM' of FIG. 2 through the assembly in a configuration where the flexible membrane is in the rest state.

FIG. 4 is another cross-section on OO' of FIG. 2, through the same assembly.

FIG. 5 shows the section shape of the flexible membrane in its maximally-deformed situation, close to the middle region.

FIG. 6 is similar to FIG. 5, but close to one of the end regions.

FIG. 7 shows two longitudinal half-sections on YOZ of FIG. 6, likewise for a situation of maximal deformation of the membrane.

FIG. 8 is a detail showing transverse ribs in an axial plane.

FIG. 9 is a detail showing longitudinal ribs.

FIG. 10 shows how the flexible membrane deforms progressively while being inflated.

FIGS. 11 and 12 are diagrammatic longitudinal sections showing two possible variants in the definition of the body and the pump membrane of the invention.

In FIG. 1, there can be seen an implantable heart-assist pump of a type that is known per se, comprising a rigid body 10 which is typically in the form of a circular cylinder (nevertheless, it is explained below that this shape is not limiting and that other circularly symmetrical shapes can be envisaged). The body is open at both ends 12 and 14 and it is inserted in the down aorta 16, with the axis of the aorta and the axis XX' of the body 10 coinciding, and with these two elements having substantially the same diameter.

The rigid body 10 contains a flexible membrane 18 which, at rest, is similar in shape to the shape of the body 10 so as to fit substantially closely to the shape thereof, and which is secured thereto at both ends 12 and 14 around the entire peripheries thereof.

Thus, between the body 10 and the membrane 18, a closed intermediate space 20 is defined that is of variable volume, and inside the membrane 18, a central space 22 is defined that is likewise of variable volume, said volume decreasing when the volume 20 increases, and vice versa.

The volume of the space 20 is increased by injecting a hydraulic fluid via at least one, and preferably via several, points 24, said points being connected via a pipe 26 to a variable pressure source 28 controlled by control electronics 30. Synchronously with beats of the heart, the electronics 30 produces variations of pressure that serve to inflate or deflate the volume 20, and correspondingly to change the volume 22 in opposite manner. This sequence of alternating inflation and deflation produces a pumping effect on the volume of blood contained in the volume 22, and thus makes it possible to reduce the effort that the heart needs to produce (a heart systole corresponding to a diastole of the assistance pump, and vice versa).

FIGS. 2 to 10 show the original design of the body and membrane assembly of the invention in greater detail.

The membrane 18 and the body 10 are secured to each other at their upstream and downstream ends at 32 via annular sectors so as to seal off the space relative to the feed duct.

The feed duct 26 is connected at 24 to an annular channel 34 (FIGS. 2 and 4) formed at the periphery of the envelope so as to facilitate the flow and the distribution of the fluid in the facing space. Advantageously, an additional duct is connected to the channel at a position diametrically opposite the duct, or a plurality of ducts are regularly distributed around the periphery of the channel, for the purpose of improving the flow and the distribution of fluid, thereby countering reaction forces that may be generated thereby and that can cause the prosthesis to move laterally. The position of the channel is preferably in the middle as shown in FIG. 2. Other channels may be disposed at different levels up and down the height of the prosthesis. The presence of the annular channel 34 is important for the purpose of minimizing headlosses in the circuit and for obtaining fast response times, and thus accurate control of membrane displacement as a function of time.

The body 10 is made as a rigid metal envelope, e.g. out of titanium, or out of a biocompatible plastics material, said envelope itself being cylindrical.

The membrane 18 is made of an elastomer material such as a silicone or a flexible and elastic polyurethane; at rest this part has the cylindrical shape as shown in FIGS. 2 to 4.

The choice of material and the definition of the flexible membrane are particularly critical since, in order to obtain sufficient lifetime (typically five years), it is absolutely essential to avoid the membrane being subjected at certain points to excessive elongation, since that leads in the end to breakage.

Polyurethane elastomers are known that are capable of operating at elongations of as much as 100% to 150% over several million cycles without being degraded. Nevertheless, to be sure of reaching, in complete safety, a minimum of several hundreds of millions of cycles without damage, it is important to keep the maximum localized elongation to which the material is subjected down to a value that is much smaller, for example deformation that does not exceed 15% at any point of the membrane.

By keeping elongation down in this way at all points, the number of cycles that can be reached without deterioration is greatly increased, thus making it possible to achieve a lifetime that is compatible with the lifetime expected of an implanted medical device.

This limitation of maximum elongation at all points of the membrane is obtained in two ways: firstly by its special shape which is described below, and secondly by adding, as necessary, ribs extending longitudinally, and optionally transversely, so as to adapt the longitudinal and transverse elasticity of the membrane so as to ensure that the imposed constraints are satisfied at all points and under all circumstances.

Whatever the amplitude of the pressure differential applied from the outside towards the inside, the shape of the membrane at all cross-sections is a star-shape (FIGS. 5 and 6), with the exception of the location 32 where it is fixed at its ends, where the envelope imposes an unchanging circular shape. The star-shape varies progressively from the ends and reaches a maximum in the middle.

FIG. 7 shows two half-sections in axial planes YY' and ZZ' at angular positions specified in FIGS. 5 and 6, for the same situation of maximum differential pressure. Thus, half-section YY' shows the profile of the membrane in the middle axial plane between two longitudinal ribs, in which plane the membrane presents its greatest concave deformation and consequently is subjected to its maximum elongation. Half-section ZZ' shows the profile of the membrane in an axial plane that includes a longitudinal rib; its concave deformation is less than in the preceding plane because of its smaller elasticity.

The membrane has ribs 36 extending longitudinally. These are regularly distributed around the periphery, there being more than two of them, and there being preferably four of them. They constitute reinforcement for the membrane for the purpose of locally reducing its longitudinal elasticity. They have the effect of guiding deformation of the membrane when it is subjected to differential pressure between the blood inside it and the hydraulic fluid outside it, thereby imposing a determined shape to the membrane.

FIG. 3 is a section showing the lumen of the membrane in the vicinity of the middle region (MM' in FIG. 2) when it is in its maximally open position. In this position, the membrane and its ribs have a rectilinear longitudinal profile. FIGS. 5 and 6 show the shape of the membrane on two sections, respectively in the vicinity of its middle region (MM' in FIG. 2), and in the vicinity of an end region (AA' in FIG. 2), when the differential pressure applied between the outside and the inside of the membrane is at a maximum, and consequently when the volume of blood contained inside the prosthesis is at a minimum.

The longitudinal elasticity of the rib and that of the portion 38 of the membrane extending between two ribs, referred to below as the "free wall", may be constant along the entire length thereof, or may be selected independently of each other along the longitudinal profile so as to model the shape of the longitudinal profile of the membrane and consequently so as to modulate the minimum volume contained inside the membrane and optimize it as a function of the maximum extension allowed by fatigue of the elastomer, e.g. by limiting maximum localized elongation to 15%.

Modelling the elasticity also makes it possible to implement asymmetrical membrane profiles between the upstream and downstream portions for the purpose of enhancing blood flow from upstream to downstream, by the asymmetry, when the membrane is contracted.

It can thus be seen how, by an appropriate shape and by the presence of ribs 36, it is possible to model the longitudinal elasticity of the membrane, which longitudinal elasticity plays an essential role in determining its longitudinal profiles, and consequently the star-shapes of its right cross-sections, in particular in the progressive transformation from the circular shape imposed at the ends to the star-shapes to be found at all other right cross-sections of the membrane.

This configuration is also particularly advantageous because it generates little turbulence, particularly when pressure is reversed, because of the unambiguous shape of the membrane.

The transverse elasticity of the free wall of the membrane is subjected to less stress. Nevertheless, this elasticity can be modulated independently of the longitudinal elasticity by means of transverse ribs that are distributed regularly or otherwise along the longitudinal profile, and that are of stiffness that is uniform or otherwise.

FIG. 8 shows transverse ribs 44 in an axial plane, preferably appearing on the outside face, so that the inside face remains smooth.

Longitudinal elasticities (ribs and free walls) and transverse elasticities (free walls) thus provide three series of independent parameters enabling the star-shaped deformation of the membrane to be adjusted optimally, in particular for the purpose of finding the minimum residual volume without causing the membrane to come into contact with itself and while maintaining an inside surface that is well-defined, smooth, free from discontinuities, and suitable for maintaining blood flow without turbulence. If the membrane were flexible but not elastic, then the star-shape could not be established in well-defined manner over a large portion of the membrane starting from its ends, which would leave the membrane in an unstable surface situation and subject to disordered movements liable to generate turbulence.

Preferably, the longitudinal and transverse reinforcing ribs are made by thickening the wall of the membrane and are obtained directly during molding of the part, with each rib preferably being situated on the outside of the membrane. Nevertheless, the longitudinal ribs are advantageously preformed on the inside as shown at 40 in FIG. 9, which is a cross-section through the rib having a concave portion 42 on its inside face, for the purpose of reducing the tensions applied to the material in the junction zone between the free wall and the rib when in the star-shaped position (FIG. 5).

The prosthesis constituted in this way is fixed upstream and downstream to the aorta by means of segments 46 (FIG. 2) of ordinary type artificial blood vessel fixed to the ends of the rigid envelope and sutured in conventional manner to the artery.

A hollow ring 48 is disposed and secured to each end of the rigid envelope, the rings 48 containing a liquid pharmaceutical substance fed from the outside via ducts 50. On its inside face, each of these rings has injectors in communication with the flow of blood and uniformly distributed around the periphery of the ring, or else a uniform injection device constituted by a porous membrane. Injection is controlled continuously, sequentially, automatically, or manually, and it is intended to administer treatment locally to oppose thromboses and expansive processes that might develop in contact with the transition zone constituted by the sutures, the segments of artificial blood vessel, the opening to the membrane, and the membrane itself.

Injection is advantageously performed by putting the drug under pressure in cyclical manner under two circumstances:

during diastolic contraction, the blood flow expelled upstream and downstream in slow and laminar manner absorbs the pharmaceutical substance on passing through the ring and sweeps the sensitive peripheral zones therewith that are located immediately downstream in the blood flow direction; and during the final stage of heart systole, the ring situated at the upstream end of the prosthesis may, conversely, direct the flow containing the pharmaceutical substance towards the inside of the membrane.

The injectors are fed from an implanted container (not shown) which is maintained under pressure either continuously or sequentially by electrical valve means controlled by the heart-assist system to which the pump belongs. The container is refilled via a subcutaneous chamber using a known technique involving a hypodermic needle.

The hydraulic fluid which is used to exert the desired back-pressure on the flexible membrane is preferably a biocompatible aqueous saline solution, for example a physiological serum, so that any leakage into the organism is not toxic.

The selection of this fluid is also important given the fact that when polymers of the kind mentioned above are used (polyurethane elastomers), they present non-negligible osmosis of the order of 2000 to 2500 times greater than that of a PTFE membrane, such that a certain amount of liquid and dissolved gases can pass through the membrane. It is therefore necessary to minimize the osmotic pressure difference.

The composition of the fluid, and in particular its salinity, must be adjusted so as to obtain equilibrium between the exchanges of components in both directions through the membrane because of its permeability, or else this equilibrium is established spontaneously by varying the volume of the fluid that can be accepted by the hydraulic flow generator.

The hydraulic fluid container advantageously comprises a septum 52 accessible percutaneously by means of a hypodermic needle in order to enable the volume of fluid and/or its salinity to be adjusted, or to enable the fluid to be emptied out.

As mentioned above, sequencing of the pump is controlled by control electronics 30 acting on the pressure source 28. The control electronics receives detection signals representative of heart activity at 54. Additionally, provision may also be made at 56 to use signals coming from a sensor 58 for sensing the position of the membrane relative to the rigid envelope in order to monitor membrane movements, and more particularly to enable the extreme positions between which it is allowed to move to be adjusted. This adjustment is performed coarsely by adjusting the volume of the fluid, and more finely and automatically by the hydraulic fluid generator.

The sensor may advantageously be constituted by one or more couples formed by a permanent magnet fixed to the membrane and a magnetic detector, preferably a magneto-resistive element fixed on the rigid envelope and facing the corresponding element.

In a variant, and for any reason, if the position of the membrane becomes abnormal and runs the risk of threatening blood flow in the aorta, a safety device operating automatically or under manual control triggers discharge of hydraulic fluid into the body of the patient, thereby reducing the external pressure exerted on the membrane and encouraging it to return to a position in which it operates acceptably, or in the limit placing it in a rest position where it is neutralized.

The pump operates as follows.

The membrane has elasticity that is substantially greater than that of the natural aorta. At each instant during which the hydraulic pressure applied to the outside face of the membrane is equal to the aorta pressure applied to its inside face, plus the component due to the elastic deformation of the membrane, the inertial forces developed by the membrane being negligible compared with those of the surrounding fluids. Consequently, starting from a rest position when it is in contact with the outer rigid envelope, the membrane is subjected in operation to a pressure difference directed from the outside towards the inside, both during its contraction movement and during the opposite movement. Contraction is produced at the beginning of heart diastole, with a duration lying approximately in the range 300 ms to 600 ms, by injecting hydraulic fluid into the intermediate space 20 between the membrane and the rigid envelope.

Initially, the ribs remain pressed against the rigid envelope, under tension between their upstream and downstream fixing points, while in the middle proton of the membrane (FIG. 10, right section MM'), the cylindrical sectors thereof extending between pairs of ribs (free walls) invert their concave sides progressively while exhibiting no elastic resistance, and consequently allowing the wall to take up a shape that is undetermined within narrow limits, until the position is reached that is opposite to the initial position and at which they come under tension, taking up a determined shape and applying force to the ribs which then move in the manner shown in FIG. 5.

The behavior in the vicinity of the ends is different because the membrane is fixed around a circle. The shape of the membrane at the ends remains essentially under the influence of the longitudinal elasticity of the free walls and under the influence of the pressure difference that develops as soon as the process of reversing the concave side has been completed.

The process of returning to rest as caused by the systolic heart flow reproduces the same phenomena as during contraction but in the opposite direction. It lasts for 150 ms to 250 ms.

Several variants or additions can be envisaged.

Thus, in order to increase the dynamic range of the membrane, i.e. the volume of blood taken in and delivered during each cycle, the membrane and the envelope may advantageously occupy in the maximum volume position the shape of a body of revolution having an outwardly curved generator line (FIG. 11) in which the middle right section of the membrane at rest is a circle but of diameter greater than that of its ends, and thus of the aorta.

In this case, the membrane is a part that is mounted so as to be naturally curved in the free state. Operation is similar to that described above.

In another variant, shown in FIG. 12, only the rigid envelope is curved, and in the rest state the membrane retains the shape of a right cylinder. Operation is similar to that of the preceding variant, except that the membrane reaches its maximum volume position by applying a reverse pressure difference starting from the rest position. This disposition has the effect of reducing the stage during which changing over the concave side of the free wall gives rise to a certain amount of instability of the surface.

I claim:

1. An implantable heart-assist pump of the back-pressure balloon type, the pump comprising:
    an essentially rigid body (10) open at both ends (12, 14) and designed to be inserted in the down aorta artery (16);
    a flexible and elastic membrane (18) in the form of a sleeve connected in sealed manner to the body at the periphery of the ends thereof so as to define firstly, between the body and the sleeve, a closed intermediate space (20) of variable volume, and secondly, inside the sleeve, a variable volume (22) through which the blood to be pumped passes; and
    means for connecting the intermediate space to a source of hydraulic fluid (28) suitable for causing the membrane to pass from a free state to a tensioned state in which it is urged radially inwards, thereby correspondingly reducing the volume through which the blood passes, and vice versa;
    the pump being characterized in that:
        between the ends of the body, the membrane is freely movable relative to the body; and
        the membrane has at least three longitudinal stiffener elements (36) uniformly distributed around the periphery of the membrane, said stiffener elements being suitable for locally reducing the longitudinal elasticity of the membrane, imposing a star-shape to the right section of the membrane in the tensioned state, which shape develops progressively between each end region and the middle region, said star-shape leaving a residual volume without the membrane coming into contact against itself.

2. The pump of claim 1, in which the longitudinal stiffener elements (36) are locally dimensioned so as to ensure that the elongation percentage of the membrane material in the tensioned state is limited at all points to a predetermined limit value as a function of the extreme profile taken up by the membrane in said state.

3. The pump of claim 1, in which the membrane further includes transverse stiffener elements (44) suitable for locally reducing the transverse elasticity of the membrane.

4. The pump of claim 1, in which the longitudinal stiffener elements (36) are ribs (40) formed on the outside space of the membrane, with the inside face having a preformed concave shape (42) in register with the ribs.

5. The pump of claim 1, in which the body further includes at least one peripheral annular enlargement in the form of an annular channel (34) open towards the membrane and connected to at least one duct (24) for delivering hydraulic fluid.

6. The pump of claim 1, in which the body is a right circular cylinder and the membrane in the free state is similar in shape to the body.

7. The pump of claim 1, in which the body is circularly symmetrical, having an outwardly curved generator line so that its middle portion has a diameter greater than the diameter of its end portions.

8. The pump of claim 7, in which the membrane in the free state has a circularly symmetrical shape corresponding to that of the body.

9. The pump of claim 7, in which the membrane in the free state is in the form of a right cylinder.

10. The pump of claim 1, in which means (48, 50) are also provided for controlled injection of a pharmaceutical agent for opposing thromboses and expansive processes that may occur locally.

11. The pump of claim 1, in which the hydraulic fluid is a biocompatible and isotonic fluid, and in which a percutaneously-accessible container (52) is provided together with means for adjusting the volume of the fluid and/or its salinity and optionally for emptying said fluid and/or discharging it into the body of the patient, should that be necessary.

* * * * *